United States Patent
McMichael (10) Patent No.: US 11,266,574 B2
(45) Date of Patent: Mar. 8, 2022

(54) BLENDERIZED DIET AND/OR BOLUS DELIVERY MANUAL PUMP

(71) Applicant: Avent, Inc., Alpharetta, GA (US)

(72) Inventor: Donald McMichael, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 99 days.

(21) Appl. No.: 16/112,964

(22) Filed: Aug. 27, 2018

(65) Prior Publication Data

US 2020/0060944 A1   Feb. 27, 2020

(51) Int. Cl.
*A61J 15/00*   (2006.01)
*A61M 5/142*   (2006.01)
*A61M 5/145*   (2006.01)

(52) U.S. Cl.
CPC ................... *A61J 15/0076* (2015.05)

(58) Field of Classification Search
CPC ............ A61J 15/0076; A61M 5/14526; A61M 2205/073; A61M 2205/075; A61M 5/14236; A61M 2005/14513; A61M 2005/14533; A61M 2005/2026; A61M 5/2046; A61M 5/315; A61M 5/31565; A61M 5/31575
See application file for complete search history.

(56) References Cited

U.S. PATENT DOCUMENTS

| | | | |
|---|---|---|---|
| 2,880,913 A * | 4/1959 | Peyron | B65D 35/30 222/214 |
| 5,993,422 A | 11/1999 | Schafer | |
| 7,172,085 B2 | 2/2007 | Beaudette | |
| 8,623,323 B2 | 1/2014 | Holahan | |
| 9,186,193 B2 | 11/2015 | Kleiner et al. | |
| 9,375,741 B2 | 6/2016 | Turner | |
| 2004/0188372 A1 | 9/2004 | Ruth et al. | |
| 2006/0224106 A1* | 10/2006 | Honchel | A61J 15/0076 604/37 |
| 2007/0106232 A1 | 5/2007 | Rider, II et al. | |
| 2008/0195047 A1* | 8/2008 | Price | A61J 15/0015 604/151 |
| 2008/0208117 A1 | 8/2008 | Steinman et al. | |
| 2009/0036873 A1 | 2/2009 | Nielsen et al. | |

(Continued)

FOREIGN PATENT DOCUMENTS

| | | |
|---|---|---|
| GB | 2525370 A | 10/2015 |
| JP | 2010099406 A | 5/2010 |

OTHER PUBLICATIONS

International Search Report and Written Opinion for PCT/US2019/046983, dated Nov. 20, 2019, 16 pages.

(Continued)

*Primary Examiner* — Lauren P Farrar
*Assistant Examiner* — Hamza A Darb
(74) *Attorney, Agent, or Firm* — Dority & Manning, P.A.

(57) ABSTRACT

Delivery pumps for providing a bolus or blenderized diet to enterally fed mammals are provided. A delivery pump according to the present disclosure is manually operated, and does not require mechanically powered operation. A delivery pump according to the present disclosure also has a size sufficient to contain an entire bolus or blenderized diet feeding, and is shaped to allow filling of the reservoir with a bolus or blenderized diet by a user. The present disclosure also includes a method of providing a bolus or blenderized diet to a mammal.

15 Claims, 7 Drawing Sheets

(56) References Cited

U.S. PATENT DOCUMENTS

| | | |
|---|---|---|
| 2011/0004161 A1 | 1/2011 | Ito |
| 2012/0076914 A1 | 3/2012 | Langford |
| 2014/0035604 A1 | 2/2014 | Paul et al. |
| 2015/0025457 A1 | 1/2015 | Moberg et al. |
| 2016/0074577 A1 | 3/2016 | Neta et al. |
| 2016/0106551 A1 | 4/2016 | Grimberg, Jr. et al. |
| 2016/0296423 A1* | 10/2016 | Ruda .................. A61J 15/0076 |
| 2016/0339172 A1 | 11/2016 | Michaud et al. |
| 2016/0361524 A1 | 12/2016 | Qaysi |

OTHER PUBLICATIONS

International Search Report and Written Opinion dated Nov. 20, 2019, from International Application No. PCT/US2019/046983, 12 pages.

International Preliminary Report on Patentability dated Mar. 11, 2021, from International Application No. PCT/US2019/046983, 9 pages.

* cited by examiner

BLENDERIZED DIET AND/OR BOLUS DELIVERY MANUAL PUMP

BACKGROUND

Numerous situations exist in which anatomical structures of the human body need to be catheterized through an artificial stoma to achieve a desired medical goal. Relatively common situations are for drainage of retained fluids and administering nutritional solutions or medicines directly into the stomach or intestines. For these situations a stoma is formed percutaneously and an indwelling device is placed through the stoma. By way of example the surgical opening and/or the procedure to create a stoma spanning between the stomach or intestinal wall and the exterior of the skin is commonly referred to as "gastrostomy." A device with a catheter component, e.g., a feeding tube, placed through such a stoma allows injection of feeding solutions through the tube to provide nutrients directly to the stomach or intestines (known as enteral feeding).

As indicated above, there are a variety of instances in which it may be necessary to use a catheter, one of which is the not uncommon reaction following major surgery in which a patient's stomach function is impaired for a period of time. In addition to the need to supply or supplement the body with a certain level of nutrients and the like following surgery as well as in other instances of impaired or limited gastric functionality, a further issue is that an unfed gut can become a source of bacteria that gets into the bloodstream. These types of problems may be resolved by the introduction of nutrients through an enteral feeding device tube properly inserted through the patient's abdominal wall, gastric wall, pylorus, duodenum, and/or into the jejunum beyond the Ligament of Treitz.

However, particularly outside of a hospital or direct care situation, a patient or the pateint's caretaker may wish to feed a blenderized diet or thick feed through the enteral feeding device tube. While many, if not all, enteral feeding devices utilize a standard connection, such as an ENFit™ connector on an external portion of the abdomen, many syringes are not sized or formed to deliver an entire feeding session of blenderized or thick food. Due to the limited choices for delivery, many patients utilize large animal syringes which require funnels or other apparatus to fill the syringe, or refill standard syringes up to 7-10 times per feeding session. Such a process is time consuming as well as unsanitary for the patient. Moreover, when filled, the rate of delivery using standard syringes can often be difficult to control.

Therefore, it would be advantageous to provide a blenderized diet or delivery pump that would overcome some of the noted deficiencies. For instance, it would be beneficial to provide a blenderized diet or delivery pump with a reservoir sized to contain an entire bolus feeding session. Further, it would be an advantage to have a reservoir that can be easily filled and/or cleaned, such as a reservoir that may be filled and stored for later use. In a further embodiment, a filling or cleaning process may be further improved by having a removable pump head in addition to the improved sizing. It would also be beneficial to have a blenderized diet or delivery pump that can be exclusively, or at least partially, manually pumped or pressurized. It would also be advantageous to have a blenderized diet or delivery pump with a plunger to facilitate even pressure, such as a removable plunger in one embodiment. Moreover, it would be advantageous to have a pump and/or plunger that allows greater control over the speed of delivery of the bolus.

SUMMARY

Aspects and advantages of the invention will be set forth in part in the following description, or may be obvious from the description, or may be learned through practice of the invention.

The present disclosure is generally directed to a delivery pump for the delivery of a blenderized diet and/or bolus. The delivery pump includes a reservoir, a removable pump head assembly, and a plunger. The reservoir has a tip and a size sufficient to contain an amount of from about 100 milliliters to about 500 milliliters of a liquid or semi-solid composition, where the tip is configured to releasably attach the reservoir to an enteral feeding device. Further, the plunger is configured to move in a substantially linear direction upon manual operation of the removable pump head assembly.

In a further embodiment, the removable pump head assembly includes a manual air pump. Additionally, the manual air pump is configured to produce compressed air in the reservoir in an embodiment. Moreover, in a further embodiment, the compressed air pushes the plunger in the substantially linear direction toward the tip of the reservoir. In one embodiment, the plunger contacts the liquid or semi-solid composition, and the compressed air is separated from the liquid or semi-solid composition by the plunger.

Additionally or alternatively, the removable pump head assembly includes a manual pump bulb. In one embodiment, the manual pump bulb is configured to produce compressed air in the reservoir such that the compressed air moves the plunger in the substantially linear direction toward the tip of the reservoir.

In yet a further embodiment, the reservoir has a diameter of from about 25 millimeters to about 75 millimeters. In an additional embodiment, the diameter of the reservoir is from about 35 millimeters to about 65 millimeters. Furthermore, in an additional or alternative embodiment, the reservoir has a size sufficient to contain an amount of the liquid or semi-solid composition of about 100 milliliters to about 500 milliliters. In one embodiment, the plunger comprises a hard plastic or a balloon.

The present disclosure also generally includes a method of feeding a mammal utilizing an enteral feeding device. The method includes placing an amount of a liquid or semi-solid composition into a blenderized diet and/or bolus delivery pump. The blenderized diet and/or bolus delivery pump includes a reservoir, a removable pump head assembly, and a plunger. The reservoir has a tip and a size sufficient to contain an amount of from about 100 milliliters to about 500 milliliters of a liquid or semi-solid composition, where the tip is configured to releasably attach the reservoir to an enteral feeding device. The method further includes manually operating the removable pump head assembly such that the plunger moves in a substantially linear direction toward a distal end of the reservoir, such that a liquid a semi-solid composition is pushed from the reservoir to the enteral feeding device.

In one embodiment, the method may include a removable pump head assembly that generates compressed air when operated by a user. Additionally or alternatively, the compressed air moves the plunger in the substantially linear direction towards a distal end of the reservoir. In yet a further embodiment, the plunger pushes the liquid or semi-solid composition from the reservoir to the enteral feeding device when the plunger is contacted by the compressed air.

In an additional or alternative embodiment, the method may include placing an amount of from about 100 milliliters to about 500 milliliters of the liquid or semi-solid composition into the reservoir. Further, in an embodiment, at least about 80% of the amount of the liquid or semi-solid composition is pushed from the reservoir to the enteral feeding device.

In yet a further embodiment, the method may include a removable pump head assembly that only utilizes manual operation to move the plunger. Additionally or alternatively, the removable pump head assembly may be separated from the reservoir after the liquid or semi-solid composition has been pushed from the reservoir. In one embodiment, the removable pump head assembly is operated by squeezing a pump handle.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Moreover, the particular naming of the components, capitalization of terms, the attributes, data structures, or any other programming or structural aspect is not mandatory or significant, and the mechanisms that implement the invention or its features may have different names, formats, or protocols. Also, the particular division of functionality between the various components described herein is merely exemplary and not mandatory; functions performed by a single component may instead be performed by multiple components, and functions performed by multiple components may instead performed by a single component.

According to the present disclosure, an enteral feeding device may generally refer to an enteral feeding device, such as a feeding tube, that has been inserted into a mammal (e.g. a human). Further the term "liquid or semi-solid composition" may be used to refer to the consistency of a bolus or blenderized diet as discussed above. For instance, a bolus or blenderized diet according to the present disclosure may utilize a fairly liquid type composition, or a thick feed type blenderized diet, or alternatively, may be referred to as an inconsistent texture feed, as may be generally known in the art. Further, in one embodiment, the viscosity of the bolus or blenderized diet may be from about 25 cps to about 1000 cps, such as from about 50 cps to about 900 cps. However, as discussed above, the present disclosure intends that the bolus or blenderized diet may include all viscosities generally encompassed by the term "thick".

The present invention may be used with a non-vascular catheter device, e.g., an enteral feeding device or the like, having a catheter tube, an external retainer (e.g., base deployed outside the human body), and an indwelling retainer that is deployed within a lumen or cavity of a patient's body (i.e., a non-vascular lumen or cavity of the body such as, for example, a gastric lumen, jejunum, peritoneal cavity or the like). For example, the indwelling retainer may be a retention mechanism of the catheter device that prevents the catheter device from being pulled out of the patient, and the indwelling retainer may be inserted into the body lumen through a stoma. The insertion through the stoma may be from outside the body or it may be performed from inside the body using endoscopic techniques. In this context, the term "insertion" should be understood as putting in or introducing the catheter tube in place in a stoma so that the base is deployed outside the human body and the indwelling retainer is deployed within a non-vascular lumen or cavity. Generally speaking, the catheter device is an enteral feeding device such as, for example, a configurable PEG (percutaneous endoscopic gastrostomy) or LPG (low-profile gastronomy) device.

Generally speaking, the present disclosure is directed to a delivery pump for delivering a blenderized diet and/or a bolus to a mammal through an enteral feeding device. Particularly, referring to FIG. 1, such a delivery pump 100 may have a reservoir 102 that has a size sufficient to contain an entire bolus or blenderized meal 109. For instance, a reservoir 102 according to the present disclosure may be sized such that the bolus or blenderized meal 109 is placed into the reservoir 102 and delivered to the mammal in a single filling of the reservoir, and does not require multiple filling steps in order to feed a mammal an entire bolus or blenderized meal 109. Furthermore, a delivery pump 100 according to the present disclosure may be at least partially, if not fully operable by hand. In such an embodiment, the delivery pump 100 may not require any machine operated function, such as an electromechanical force, and may rely fully, or at least partially, upon manual operation. Further yet, a delivery pump 100 according to the present disclosure may also allow a user to control the rate of delivery of a bolus or blenderized meal 109 to a mammal with greater precision. For example, in a delivery pump 100 according to the present disclosure, compressed air may not contact the bolus or blenderized meal 109 directly, and instead, the compressed air may move a plunger 106 which presses the bolus or blenderized meal 109 through the tip 108 of the reservoir. Such a plunger 106 may have a pressure gauge 110 or increment guide such as graduations 112, which allows a user to better control the rate of delivery of the bolus or blenderized meal. Such advantages will now be discussed in greater detail.

For instance, in one embodiment, the reservoir may have a size such that the reservoir may contain an amount of a liquid or semi-solid composition of about 100 milliliters to about 500 milliliters, such as an amount of from about 150 milliliters to about 450 milliliters, such as an amount of from about 200 milliliters to about 400 milliliters, such as an amount of from about 275 milliliters to about 375 milliliters, such as an amount of from about 300 milliliters to about 350 milliliters. Of course, as may be well known in the art, one milliliter is equivalent to one centimeter cubed ($cm^3$). Therefore, the preceding liquid volume measurements may also correspond to an internal volume of the reservoir in cubic centimeters.

Figure 1:
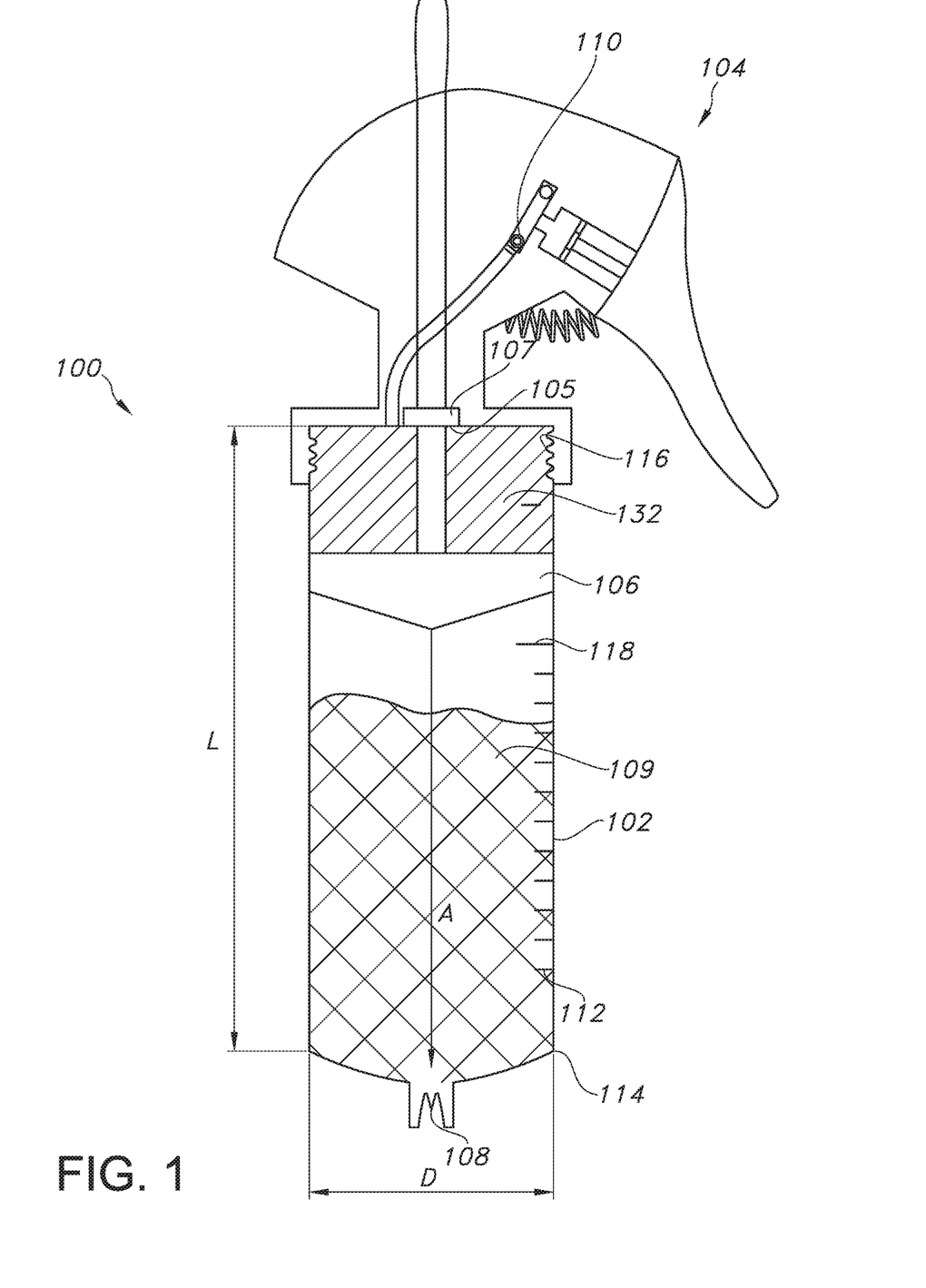
FIG. 1 is a view of a delivery pump of the present disclosure.

While the volume of a liquid or semi-solid composition may define the entire volume of the reservoir, it is also contemplated by the present disclosure that the reservoir be sized to contain such a volume of a liquid or semi-solid composition and also contain a plunger and/or portions of the removable pump head assembly which will be discussed further below. In such an embodiment, it is contemplated that the reservoir may contain any of the volumes discussed above below a fill level, and have a portion above a fill level sufficiently sized to contain a plunger and/or portions of the removable pump head. Referring to FIG. 1, in such an embodiment, the reservoir 102 may have a length L between a distal end 114 of the reservoir 102 that is adjacent to a tip 108, and a proximal end 116 of the reservoir 102 configured to attach to a removable pump head assembly 104, both of which will be discussed in greater detail below. In such an embodiment, a fill line 118 may be nearer to the proximal end 116 than the distal end 114. Particularly, a liquid or semi-solid composition may be placed into the reservoir 102, and begins filling the reservoir 102 from a distal end 114 adjacent to the tip 108. Thus, a reservoir 102 may be filled from a distal end 114 towards a proximal end 116. In such an embodiment, a fill line 118 may be located at about the midpoint of the reservoir 102, such as at a point about 60% or more of the length L of the reservoir 102 from the distal end 114 to the proximal end 116, such as a point of about 65% or more, such as a point of about 70% or more, such as a point of about 75% or more, such as a point of about 80% or more of the length L of the reservoir 102 from the distal end 114 to the proximal end 116. However, in an embodiment, it is also contemplated that the entire internal volume of the reservoir 102 be defined according to the liquid or semi-solid amounts discussed above, such that the amounts discussed above define a volume sufficient to contain the bolus or blenderized diet 109 and the plunger and/or pump head assembly.

Continuing to refer to FIG. 1, in addition to forming a reservoir 102 that may contain a volume of a liquid or semi-solid composition as discussed above, a delivery pump 100 according to the present disclosure contemplates a reservoir 102 having a length L and a diameter D, while enabling a size as discussed above, that are selected in order to provide greater ease in the handling of the delivery pump 100. For instance, a reservoir according to the present disclosure may have a sufficiently large diameter D so as to increase the surface area, allowing greater air pressure to form in the reservoir 102 upon operation of the delivery pump 100, with less effort by a user. Further a larger diameter D may allow a reservoir 102 with a shorter length L to be used, allowing the delivery pump 100 to be less unwieldy and thus easier for a user to attach to an enteral feeding device. Furthermore, a reservoir 102 with a larger diameter D and a shorter length L may provide a reservoir 102 that is easier to fill without spilling the liquid or semi-solid composition, allowing for a cleaner and more sanitary delivery.

Thus, in one embodiment, a reservoir according to the present disclosure may have a diameter D of from about 10 millimeters to about 125 millimeters, such as from about 15 millimeters to about 100 millimeters, such as from about 20 millimeters to about 80 millimeters, such as from about 25 to about 75 millimeters, such as from about 35 millimeters to about 65 millimeters.

Additionally, a reservoir according to the present disclosure may have a length L of from about 100 millimeters to about 1100 millimeters, such as from about 150 millimeters to about 750 millimeters, such as from about 200 millimeters to about 500 millimeters, such as from about 200 millimeters to about 450 millimeters.

Therefore, as a bolus or blenderized meal 109 for a mammal generally has a volume of from about 100 milliliters to about 500 milliliters, in one embodiment, a reservoir 102 sized according to the present disclosure may be able to contain an entire bolus or blenderized meal 109, eliminating the need to refill the reservoir multiple times for a single feeding. Further, a reservoir 102 having a diameter D according to the present disclosure may eliminate the need for a funnel or additional pouring devices, allowing for easier and more sanitary filling of the reservoir 102. Further still, a reservoir 102 having a size according to the present disclosure may also be easier to handle and attach to an enteral feeding device, as the shorter length L allows the delivery pump 100 to be more easily handled and connected.

Figure 2:
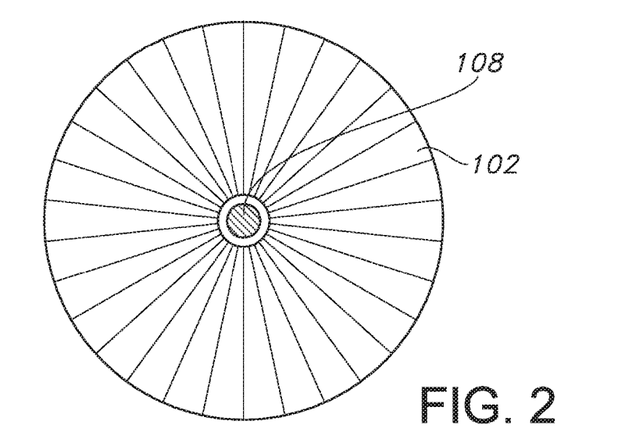
FIG. 2 is a view of a tip for connecting to an enteral feeding device of the present disclosure.

Moreover, referring to FIGS. 1 and 2, a reservoir 102 according to the present disclosure may have a tip 108 that is easily connected to an enteral feeding device. While the tip 108 may have any shape or size that allows passage of the liquid or semi-solid composition from the reservoir to the enteral feeding device, in one embodiment, the tip 108 may have a shape, material, and/or design that is compatible with an ENFit™ system and/or compatible with such as a system as generally referred to by ISO 80369-3. Thus, in one embodiment, the tip 108 may be designed as an ENFit™ connector. However, as discussed, the tip 108 may also have any dimension necessary to connect to other enteral feeding devices that allows passage of the bolus or blenderized meal from the reservoir 102 of the delivery pump 100, to the enteral feeding device.

A reservoir according to the present disclosure may be formed of any material generally known in the art for the formation of syringe. For instance, in one embodiment, the reservoir may be formed from an ISO/healthcare compliant hard plastic, such as a polypropylene, a co-polyester, or combinations thereof, as well as other materials as generally known in the art. In a further embodiment, the hard plastic may be selected to be a "dishwasher safe" plastic, such that the reservoir may be cleaned in a residential dishwasher, for example polypropylene or a Tritam™ copolyester. Thus, in one embodiment, a hard plastic may be selected, or may be treated, such that the chosen plastic may be able to withstand temperatures of from about 120° F./48.8° C. to about 180° F./82.2° C., without deforming or losing its integrity. Therefore, in an embodiment, a reservoir according to the present disclosure may be used for more than one bolus or blenderized diet delivery, but may still be disposable or semi-disposable.

Moreover, as generally shown in FIG. 1, the material selected to form the reservoir 102 may be transparent, or opaque, or alternatively, may be solid (not shown). In one embodiment, the material selected to form the reservoir 102 may be transparent or opaque, in order to allow a user to further gauge the rate of delivery of the bolus or blenderized diet. For instance, in such an embodiment, a user may be able to see the level of the bolus or blenderized diet through the transparent or opaque material, such that the graduations 112 may be used to measure an amount of the bolus or blenderized diet delivered to a mammal over a period of time. Of course, in a further embodiment, a solid material may be used such that the reservoir 102 is not transparent, and an amount or rate of delivery may be measured using a pressure gauge 110, though it should be noted that the pressure gauge 110 may still aid a user in delivering a bolus or blenderized diet when using an opaque or transparent material.

Figure 3A:
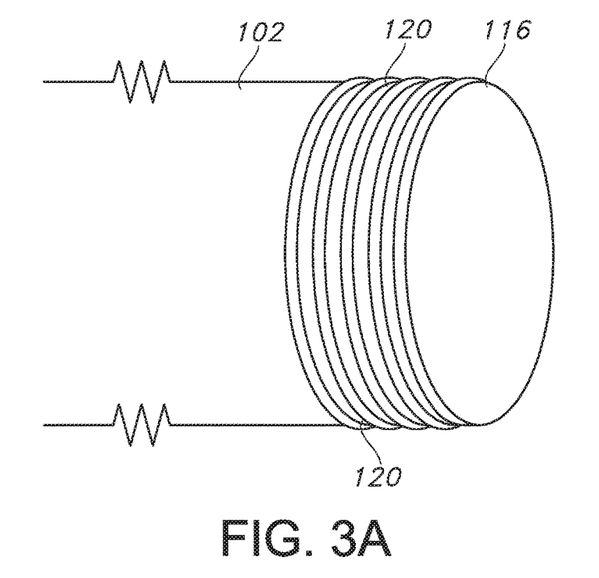
FIG. 3a is a view of a portion of a reservoir of the present disclosure.
Figure 3B:
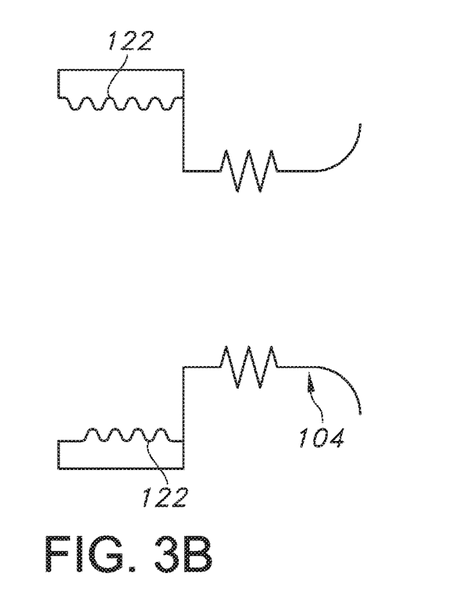
FIG. 3b is a view of a portion of a removable pump head assembly of the present disclosure.

Furthermore, referring to FIGS. 1 and 3, a reservoir 102 according to the present disclosure may also have a proximal end 116 that is configured to be releasably attached to a removable pump head assembly 104 which will be discussed in greater detail below. For instance, the proximal end 116 may have thread or thread grooves 120 for engaging complementary thread grooves 122 on a pump head assembly 104. In a further embodiment which is not illustrated, a lip for a "snap fit" type connection may be included on the reservoir 102, or any other releasable type connection known in the art, instead of thread grooves, that allows a seal to be formed between the reservoir 102 and the pump head assembly 104 may be used. Particularly, it is desirable that the connection configuration be a configuration that may easily be engaged and disengaged by a user. Though not shown, the proximal end 116 of the reservoir may also be configured to be used with a lid or cap. In such a manner, the configuration used to attach the pump head may also be used to releasably attach a lid or cap, such that the reservoir may be filled in advance and stored for later use.

Therefore, regardless of the type of pump head assembly used, in an embodiment according to the present disclosure, the removable pump head assembly 104 has an attachment configuration compatible with the attachment configuration of the proximal end 116 of the reservoir 102. For instance, in an embodiment where the proximal end 116 of the reservoir 102 has threads or thread grooves 120, the pump head assembly 104 may have a compatible set of threads or thread grooves 122. Further, in an embodiment where the proximal end 116 of the reservoir 102 has a lip (not shown), the pump head assembly 104 may contain a snap fit type assembly. Of course, other attachment configurations as are known in the art may be used, and compatible attachment configurations may be included on the pump head assembly and on the reservoir.

Regardless of the attachment configuration selected, the removable pump head assembly 104 may contain an opening 105 to accommodate a plunger 106. Further, the removable pump head assembly 104 may contain a plunger seal 107, in or on the opening 105. Such a seal 107 may be formed of any material generally known in the art, such as a deformable plastic or thermoplastic. Regardless of the material selected for the seal 107, it should be capable of forming an airtight seal with the plunger 106. Furthermore, the seal 107 may be located outside of the reservoir 102, such as on an external portion of the removable pump head assembly 104, or may be incorporated into the opening 105 itself, or may be included on an interior portion of the removable pump head assembly 104 such that the seal is located in the reservoir 102 when the removable pump head assembly 104 is attached to the reservoir 102, or may be included in a combination of the locations. Regardless, the seal 107 is oriented and formed from a material sufficient to provide a seal between the plunger 106 and the removable pump head assembly 104.

Notwithstanding the type of seal 107 selected, a plunger 106 and a seal 107 are selected that allow compressed air 132 to be contained in the reservoir 102 between the proximal end 116 of the reservoir 102 and the plunger 106. For instance, the plunger 106 may have a shape, and may be formed from a material, such that the plunger 106 forms a seal between the outer edge of the plunger 106 and the inner wall of the reservoir 102. In such a manner, the plunger may be configured to separate the compressed air 132 from a bolus or blenderized diet 109 that is trapped between the distal end 114 of the reservoir 102 and the plunger 106. Using such an orientation and plunger 106 allows greater control over the delivery of the bolus or blenderized diet 109. For instance, by serving as a barrier between the compressed air 132 and the bolus or blenderized diet 109, the plunger 106 may push the bolus or blenderized diet 109 from the reservoir 102 in a fairly smooth, and generally linear manner, such as generally shown by arrow A. Particularly, instead of compressed air pressing against the bolus or blenderized diet 109, which may cause uneven flow or air bubbles, the plunger 106 may move in a generally linear direction A based upon the pressure formed from the compressed air 132. Therefore, a plunger 106 formed according to the present disclosure may provide a user with a more uniform and even manner of delivering a bolus or blenderized diet 109.

Furthermore, a plunger 106 may have a rate of delivery that is easier for a user to control. Particularly, utilizing the graduations 112 and/or the pressure gauge 110, a user may monitor the rate of delivery of the bolus or blenderized diet 109. As the plunger 106 moves in a fairly steady and generally linear manner A, a user may be more easily able to determine a rate of delivery of the bolus or blenderized diet 109. Further, using a pressure gauge 110, a user may determine the pressure in the reservoir 102, and may release pressure via the pressure gauge 110, or may suspend operation of the pump head assembly, until a lower pressure and/or lower rate of delivery is obtained. For instance, as the air pressure 132 in the reservoir 102 is a function of the volume of the reservoir between the proximal end 116 of the reservoir 102 and the plunger 106, a user may allow the plunger 106 to move towards a distal end 114 without introducing further compressed air until a desired lower pressure is reached.

Figure 4A:
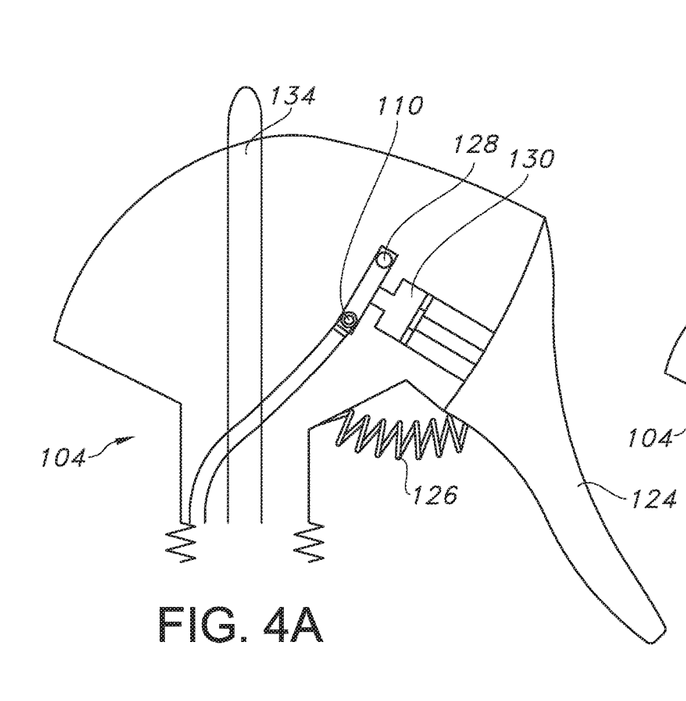
FIG. 4a is a close up cross-sectional view of a portion of a removable pump head assembly of the present disclosure.
Figure 4B:
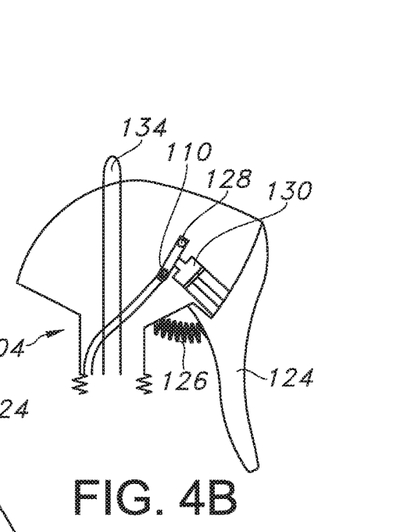
FIG. 4b is a close up cross-sectional view of a portion of the removable pump head assembly of FIG. 4a in a depressed position.

Regardless of the plunger 106 and seal 107 used, in one embodiment, the pump head assembly 104 may include an air pump type head assembly. For instance, referring to FIGS. 4a and 4b, a delivery pump of the present disclosure may include a pump head assembly 104. The air pump type head assembly may include a hand pump 124, which may be grasped with the hand or fingers of a user, and squeezed toward the head assembly 104, until the hand pump 124 is in a depressed position, such as the position shown in FIG. 4b. Return spring 126 may urge the hand pump 124 back into the original position, shown in FIG. 4a, after the user releases his or her hand or fingers. By repeatedly squeezing the hand pump 124 into a depressed position and allowing the hand pump 124 to return to the starting position, air may be pumped into the reservoir 102 through the head assembly 104 via an air intake hole 128 by activating and releasing piston 130. Thus, the air brought into the delivery pump 100 via the air intake hole 128 is compressed in the upper portion 132 of the reservoir 102, as shown in FIG. 1. Optionally, a pump head assembly, such as the air pump type head assembly shown in FIGS. 1, 4a, and 4b, may include an alignment rod 134, which may allow a user to more easily attach the head assembly 104 to the reservoir. However, regardless of the exact configuration, an air pump type head assembly, such as that generally shown in FIGS. 1, 4a, and 4b of the present disclosure, may operate solely by manual power, and may not rely upon any mechanically powered operation.

Figure 5A:
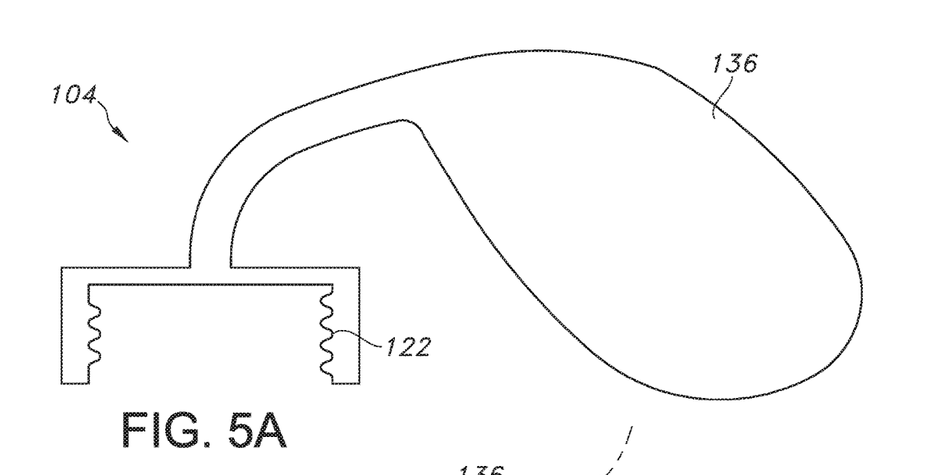
FIG. 5a is a close up view of a removable pump head assembly of the present disclosure.
Figure 5B:
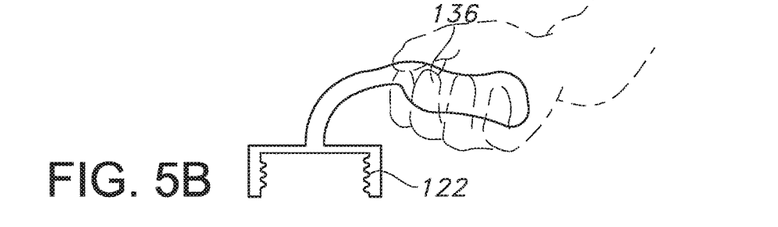
FIG. 5b is a close up view of the removable pump head assembly according to FIG. 5a in a depressed position.

In an alternative embodiment, the pump head assembly may include a pump bulb type head assembly such as generally shown in FIGS. 5a and 5b. In such an embodiment, the delivery pump may include a pump bulb 136 as the head assembly 104. In such an embodiment, a user may grasp the pump bulb 136 with their hand or fingers, and squeeze the bulb into a depressed configuration, such as generally shown by FIG. 5b. By repeatedly squeezing the pump bulb 136 into a depressed configuration and allowing the pump bulb 136 to return to the starting position, such as generally shown in FIG. 5a, air may be pumped into the reservoir 102 through the head assembly 104, and compressed in reservoir 102, by depressing and releasing pump bulb 136.

Figures 6A, 6B:
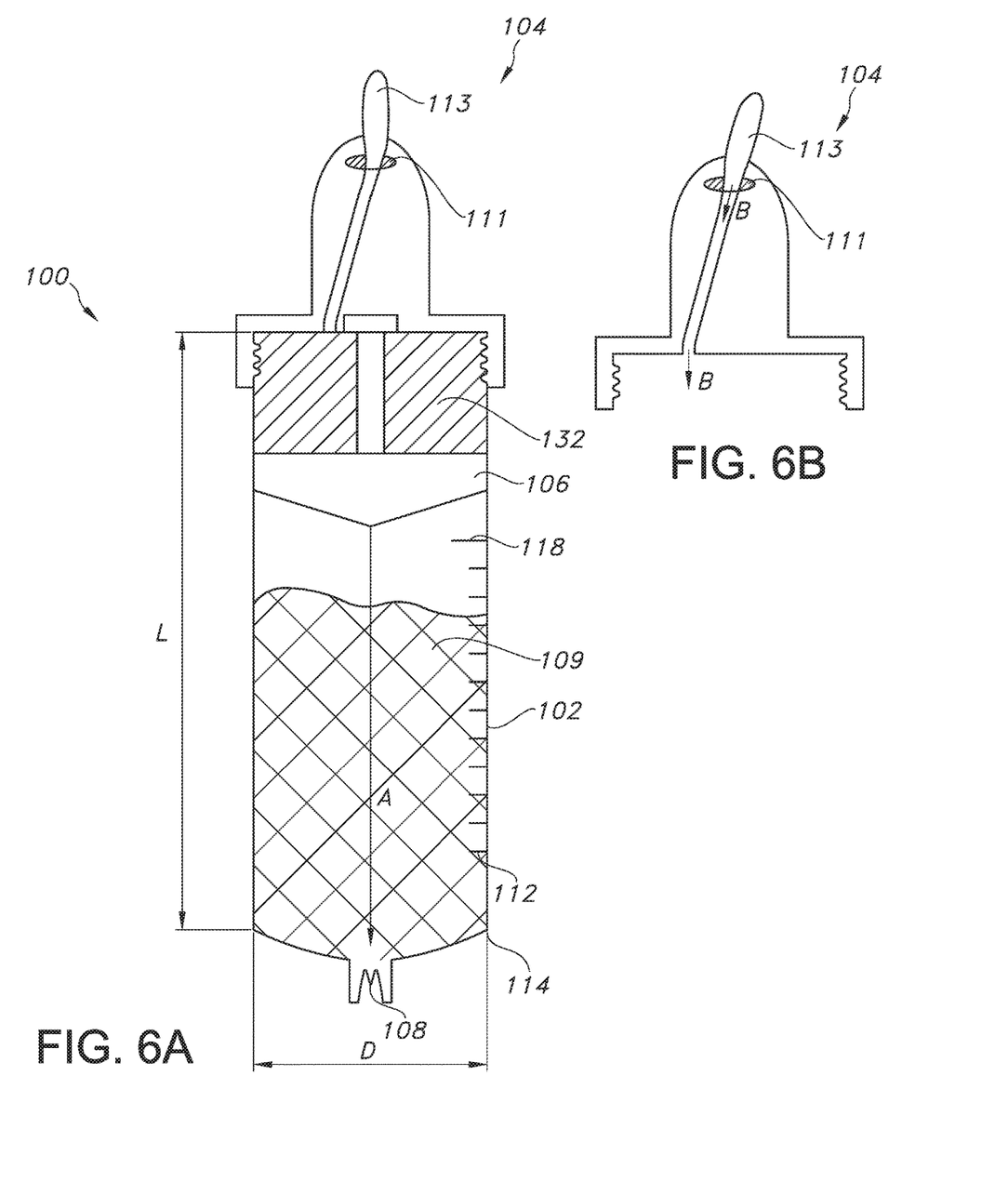
FIG. 6a is a view of a removable pump head assembly of the present disclosure.
FIG. 6b is a view of the removable pump head assembly according to FIG. 6a in a depressed position.

Additionally, in a further embodiment, as generally shown in FIGS. 6a and 6b, a $CO_2$ bullet 111 may be used alone or in conjunction with any of the pump heads discussed above. For instance, the $CO_2$ bullet 111 may interact with a lever 113, such that when the lever 113 is depressed, such as shown in FIG. 6b, the $CO_2$ bullet may release oxygen into the reservoir 102, generating compressed air 132 in the reservoir 102. For instance, arrows B may generally show air being released from the $CO_2$ bullet 111 towards a reservoir (pictured in FIG. 6A).

Figure 7:
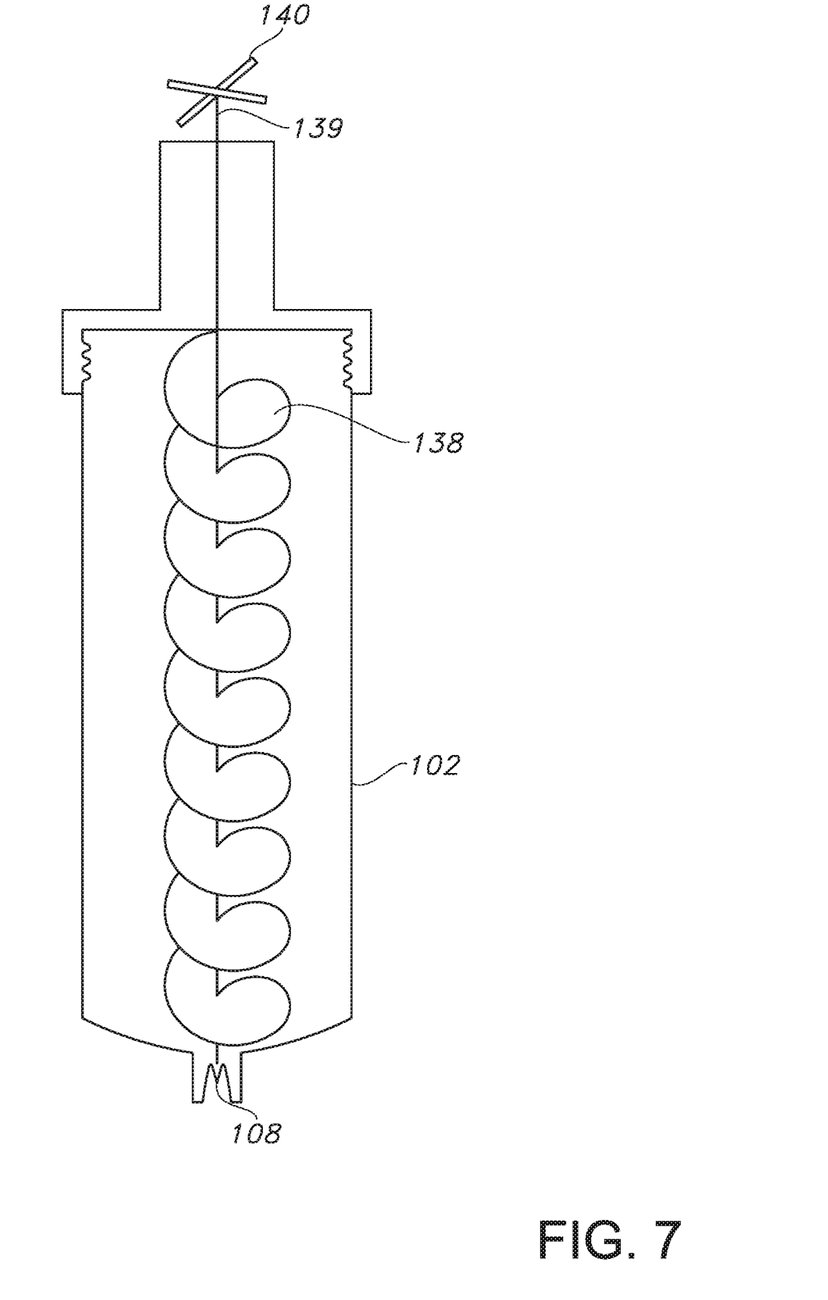
FIG. 7 is a cross-sectional view of a delivery pump according to the present disclosure.

In yet a further embodiment, such as generally shown by FIG. 7, no air pressure may be used to deliver the bolus or blenderized diet, and instead, a metering screw 138 may be used. In such an embodiment, the pump head assembly may include a metering screw 138, as well as a portion of the metering screw 138 that protrudes from the reservoir 102. The protruding portion 139 of the metering screw is configured to be turned, whether by hand, such as by turning a lever or handle 140 of the protruding portion of the metering screw. Regardless, as is generally known in the art, the metering screw may deliver a metered portion of the bolus or blenderized diet to the tip 108 of the reservoir 102, providing greater predictability in the delivery of the bolus or blenderized diet.

Figures 8A, 8B:
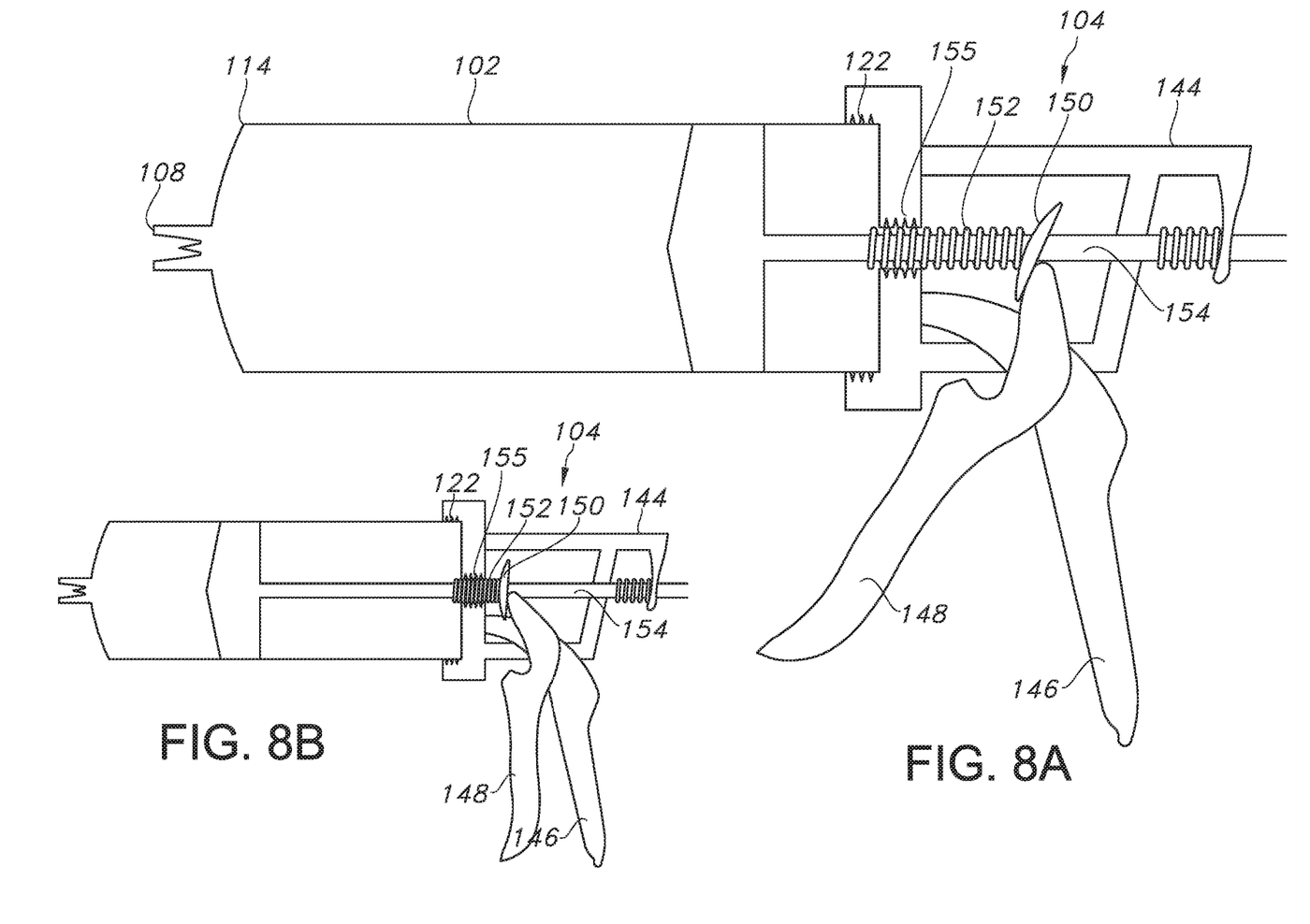
FIG. 8a is a view of a delivery pump according to the present disclosure.
FIG. 8b is a view of the delivery pump according to FIG. 8a in a depressed position.

In an additional embodiment, such as may be generally shown in FIGS. 8a and 8b, the pump head assembly may include a ratcheting plunger 144. In such an embodiment, a user may grasp a handle 146 and a lever 148 with his or her hand or fingers. A user may then use their hand or fingers to pull the lever 148 towards the handle 146. The lever 148 may contact a push bar 150 which urges a spring 152 and a plunger 154 toward a distal end 114 of the reservoir 102. The spring 152 then engages a tooth or several teeth 155 of the ratcheting plunger assembly 144, maintaining the ratcheting plunger assembly 144 in the depressed position, even after lever 148 is released and allowed to return to an original position. In such a manner, a metered portion of a bolus or blenderized diet may be released by a user squeezing a handle 146 and a lever 148 of a pump head assembly, and a second metered portion may be easily provided by repeating the motion.

Figure 9:
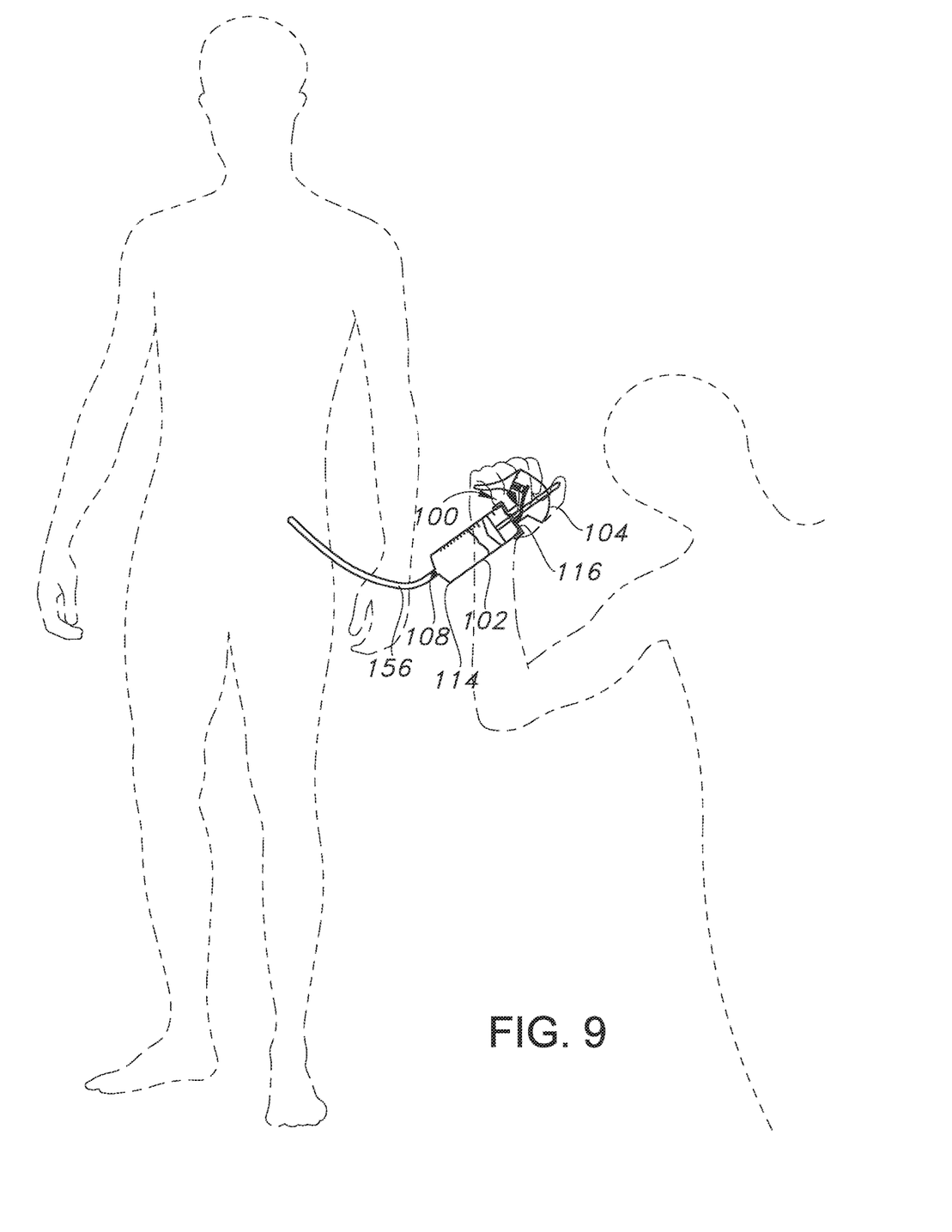
FIG. 9 is a view of a patient receiving a bolus using a delivery pump according to the present disclosure.

The present disclosure also generally contemplates the delivery of a bolus or blenderized diet to a mammal. For instance, referring to FIG. 9, a delivery pump 100 of the present disclosure may be connected via the tip 108 to an enteral feeding device 156. Regardless of the pump head assembly 104 selected, a user may operate the pump head assembly to push a bolus or blenderized diet from a proximal end 116 of the reservoir towards the distal end 114 and the tip 108 of the reservoir 102. When sufficient pressure has been provided to the bolus or blenderized diet, the bolus or blenderized diet may be pushed through the tip 108 into the enteral feeding device 156. The bolus or blenderized diet may then be provided into a stomach or small intestine of the mammal via the enteral feeding device 156. The user may continue providing pressure to the delivery pump 100 until the plunger, has reached the distal end 114 of the reservoir 102 and/or all of the bolus or blenderized diet has been pushed through the tip 108 into the enteral feeding device 156.

Thus, in such a manner, a user may easily delivery a bolus or blenderized diet using a delivery pump. Particularly, the delivery pump may provide sufficient and even pressure to deliver a liquid or semi-solid bolus or blenderized diet with a fairly high viscosity and/or thickness through a syringe in a single use. In such a manner, a user may only need to fill a reservoir of a delivery pump according to the present disclosure a single time in order to deliver an entire bolus or blenderized meal. Furthermore, a delivery pump according to the present disclosure may also be operated at least partially, if not solely, by hand, and may not require any mechanical or automatic pump or movement. Therefore, a user may deliver a high viscosity or thickness feed, which previously had been difficult to deliver, in a single feeding session without needing to refill the reservoir, and may also be able to administer the feed in a more even and sanitary manner.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A blenderized diet and/or bolus delivery pump comprising:

a reservoir having a proximal end and a distal end, a tip located at the distal end, and a size sufficient to contain an amount of from about 100 milliliters to about 500 milliliters of a liquid or semi-solid composition, where the tip is configured to releasably attach the reservoir to an enteral feeding device;

a removable pump head assembly attached to the proximal end of the reservoir; and a plunger disposed within the reservoir;

wherein manual operation of the removable pump head assembly is configured to produce compressed air in the reservoir;

wherein the plunger is configured to be pushed by the compressed air in a substantially linear direction toward the tip of the reservoir upon the manual operation of the removable pump head assembly.

2. The delivery pump of claim 1, wherein the removable pump head assembly comprises a manual air pump.

3. The delivery pump of claim 1, wherein the plunger contacts the liquid or semi-solid composition, and the compressed air is separated from the liquid or semi-solid composition by the plunger.

4. The delivery pump of claim 1, wherein the removable pump head assembly comprises a manual pump bulb.

5. The delivery pump of claim 1, wherein a diameter of the reservoir is from about 25 millimeters to about 75 millimeters.

6. The delivery pump of claim 5, wherein the diameter of the reservoir is from about 35 millimeters to about 65 millimeters.

7. The delivery pump of claim 1, wherein the reservoir has a size sufficient to contain an amount of the liquid or semi-solid composition of about 150 milliliters to about 450 milliliters.

8. The delivery pump of claim 1, wherein the plunger comprises a hard plastic or a balloon.

9. A method of feeding a mammal utilizing an enteral feeding device comprising:

placing an amount of a liquid or a semi-solid composition into a blenderized diet and/or bolus delivery pump, the blenderized diet and/or bolus delivery pump comprising:

a reservoir having a proximal end and a distal end, a tip located at the distal end, and a size sufficient to contain an amount of from about 100 milliliters to about 500 milliliters of the liquid or semi-solid composition, where the tip is configured to releasably attach the reservoir to an enteral feeding device;

a removable pump head assembly attached to the proximal end of the reservoir; and a plunger disposed within the reservoir; and manually operating the removable pump head assembly to generate compressed air in the reservoir such that the plunger moves in a substantially linear direction toward the distal end of the reservoir.

10. The method of claim 9, wherein the plunger pushes the liquid or semi-solid composition from the reservoir to the enteral feeding device when the plunger is contacted by the compressed air.

11. The method of claim 9, wherein an amount of from about 150 milliliters to about 450 milliliters of the liquid or semi-solid composition is placed into the reservoir.

12. The method of claim 11, wherein at least about 80% of the amount of the liquid or semi-solid composition is pushed from the reservoir to the enteral feeding device.

13. The method of claim 9, wherein the removable pump head assembly only utilizes manual operation to move the plunger.

14. The method of claim 9, further comprising separating the removable pump head assembly from the reservoir after the liquid or semi-solid composition has been pushed from the reservoir.

15. The method of claim 9, wherein the removable pump head assembly is operated by squeezing a pump handle.

* * * * *